United States Patent [19]
David et al.

[11] Patent Number: 5,441,047
[45] Date of Patent: Aug. 15, 1995

[54] AMBULATORY PATIENT HEALTH MONITORING TECHNIQUES UTILIZING INTERACTIVE VISUAL COMMUNICATION

[76] Inventors: Daniel David; Zipora David, both of 52 Hashalom St., Ranana, Israel

[21] Appl. No.: 66,903

[22] Filed: May 25, 1993

Related U.S. Application Data

[63] Continuation-in-part of Ser. No. 857,470, Mar. 25, 1992, abandoned.

[51] Int. Cl.$^6$ ............................................. A61B 5/02
[52] U.S. Cl. ..................... 128/670; 128/630; 128/904; 348/93
[58] Field of Search ............... 128/670, 671, 903, 904, 128/899, 898, 774, 630; 348/13-20, 98

[56] References Cited

U.S. PATENT DOCUMENTS

| | | | |
|---|---|---|---|
| Re. 31,691 | 10/1984 | Wang | 250/213 |
| Re. 32,758 | 10/1988 | Zartman | 128/736 |
| 3,517,120 | 6/1970 | Bunting | 178/6.8 |
| 3,534,161 | 10/1970 | Friesen et al. | 178/5.6 |
| 3,588,336 | 6/1971 | Scher | 178/6.8 |
| 3,613,669 | 10/1971 | Corbin et al. | 128/2.06 |
| 3,668,307 | 6/1972 | Face et al. | 178/5.6 |
| 3,691,295 | 9/1972 | Fisk | 178/58 |
| 3,946,159 | 3/1976 | Fay | 179/2 |
| 3,978,470 | 8/1976 | McGuire | 340/324 |
| 4,051,522 | 9/1977 | Healy et al. | 358/86 |
| 4,150,284 | 4/1979 | Trenkler et al. | 250/199 |
| 4,151,407 | 4/1979 | McBride et al. | 250/199 |
| 4,203,035 | 5/1980 | Grenier | 250/363 |
| 4,237,344 | 12/1980 | Moore | 179/2 |
| 4,249,206 | 2/1981 | Roscoe | 358/86 |
| 4,258,387 | 3/1981 | Lemelson et al. | 348/14 |
| 4,524,243 | 6/1985 | Shapiro | 179/5 |
| 4,736,196 | 4/1988 | McMahon et al. | 340/573 |
| 4,768,854 | 9/1988 | Campbell et al. | 350/96.16 |
| 4,805,631 | 2/1989 | Roi du Marc et al. | 128/903 |
| 4,838,275 | 6/1989 | Lee | 128/904 |
| 4,856,864 | 8/1989 | Campbell et al. | 350/96.16 |
| 4,860,112 | 8/1989 | Nichols et al. | 358/400 |

(List continued on next page.)

FOREIGN PATENT DOCUMENTS

| | | | |
|---|---|---|---|
| 0293083 | 11/1988 | European Pat. Off. | |
| 9214397 | 9/1992 | WIPO | 128/670 |

OTHER PUBLICATIONS

Gernsback, "The Tekdoctor" Feb. 1955; Radio Electronics.

Criticare Systems, Inc., Model 507 Noninvasive Patient Monitor Specifications sheet (1991).

Electronics Engineers' Handbook, Third Edition, pp. 21-60 to 21-73 (1989).

(List continued on next page.)

Primary Examiner—William E. Kamm
Assistant Examiner—Marianne Parker
Attorney, Agent, or Firm—Banner & Allegretti, Ltd.

[57] ABSTRACT

An ambulatory (in the home) patient health monitoring system is disclosed wherein the patient is monitored by a health care worker at a central station, while the patient is at a remote location. The patient may be a person having a specific medical condition monitored or may be an elderly person desiring general medical surveillance in the home environment. Cameras are provided at the patient's remote location and at the central station such that the patient and the health care worker are in interactive visual and audio communication. A communications network such as an interactive cable television is used for this purpose. Various medical condition sensing and monitoring equipment are placed in the patient's home, depending on the particular medical needs of the patient. The patient's medical condition is measured or sensed in the home and the resulting data is transmitted to the central station for analysis and display. The health care worker then is placed into interactive visual communication with the patient concerning the patient's general well being, as well as the patient's medical condition. Thus, the health care worker can make "home visits" electronically, twenty-four hours a day.

36 Claims, 9 Drawing Sheets

U.S. PATENT DOCUMENTS

| | | | |
|---|---|---|---|
| 4,885,795 | 12/1989 | Bunting et al. | 455/5 |
| 4,922,909 | 5/1990 | Little et al. | 128/774 |
| 4,930,144 | 5/1990 | Plut et al. | 378/99 |
| 4,945,410 | 7/1990 | Walling | 358/141 |
| 4,966,154 | 10/1990 | Cooper et al. | 128/671 |
| 5,005,126 | 4/1991 | Haskin | 364/413.13 |
| 5,014,125 | 5/1991 | Pocook et al. | 358/86 |
| 5,014,267 | 5/1991 | Tompkins et al. | 370/62 |
| 5,033,112 | 7/1991 | Bowling et al. | 455/603 |
| 5,053,883 | 10/1981 | Johnson | 358/349 |
| 5,081,543 | 1/1992 | Romandi | 359/145 |
| 5,081,627 | 1/1992 | Yu | 371/29.1 |
| 5,084,828 | 1/1992 | Kaufman et al. | 364/479 |

OTHER PUBLICATIONS

FCC, Notice of Proposed Rule Making 91-16 (Mar. 4, 1991).

TV Answer, Informational Materials on Interactive Television (1991).

Bain & Co., "Interactive Video Data Services: Industry Perspectives," (Apr. 15, 1991).

Hoke Communications, Inc., Friday Report, Jan. 18, 1991.

Los Angeles Times, "Interactive TV Moves A Step Closer with FCC Proposal" (Jan. 11, 1991).

Perrin et al., "Scalp Current Density Mapping: Value and Estimation from Potential Data," *IEEE Transactions on Biomedical Engineering*, vol. 34, p. 283-288 (1987).

Y. Hasin et al., "Transtelephone Adjustment of Antiarrhythmic Therapy in Ambulatory Patients," *Cardiology* vol. 63, pp. 243-251 (1978).

S. Akselrod, et al., "Spectral Analysis of HR Fluctuations in the Evaluation of Autonomous Control During Acute Myocardial Infarction," IEEE pp. 315-318 (1985).

Y. Hasin et al., "Diagnostic and Therapeutic Assessment by Telephone Electrocardiographic Monitoring of Ambulatory Patients," *British Medical Journal*, vol. 2, pp. 609-612 (1976).

V. Mor-Avi, et al., "Effects of Myocardial Ischemia and Localized Epicardial Hypothermia on the High Frequency Content of ECG in Dogs," IEEE pp. 557-580 (1988).

"Ambulatory Monitoring Management of Cardiac Patients," D. David E. Michelson and L. Dreifus (eds.), pp. 1-4, 43-57, 73-82, 105-121, F. A. Davis Co. (1988).

Acute Coronary Care: Principles and Practice, R. Calif and G. Wagner (eds.), pp. 531-536, Martinus Nijhoff Publ. (1985).

D. David, Letter to Editor, Guidelines for Ambulatory Electrocardiography, p. 1098 (date unknown).

Akselsen, et al. "Telemedicine and ISDN," *IEEE Communications Magazine*, pp. 46-51, Jan. 1993.

T. Danielson, et al., "RATATOSK-An Adaptive User Interface to Computer-Medicated Communication," Message Handling Systems and Application Layer Communication Protocols, Zurich, Oct. 3-5, 1990. Also available as TF-lecture F16/90, Kjeller, Norwegian Telecom Research.

G. Hartviksen and S. Pedersen, "Remote Endoscopy of Otorhinolaryngology Patients," In A. Katzir (ed.) *Optical Fibers in Medicine VII, SPIE Proc.* 1649, 1992.

C. Higgins, E. Dunn, and D. Conrath, "Telemedicine: A Historical Perspective," *Telecommunications Policy*, Dec. 1984.

I. Nordrum, et al. 1991. "Remote Frozen Section Service: A Telepathology Project in Northern Norway," *Human Pathol.* vol. 22, pp. 511-518, 1991.

U. Holand, S. V. Tetzchner, and K. Steindal, "Two Field Trials with Videophones in Psychiatric and Habilitative Work," In S. V. Tetzohner (ed.), *Issue in Telecommunication and Disability*, COST 219 (1991).

T. Sund, E. Rinde, and J. Stormer, 1991, "Full-scale Replacement of a Visiting Radiologist Service with Teleradiology," in H. U. Lemke, et al., (ed.), *Computer Assisted Radiology, Proc. Int. Symp. CAR-91*. Berlin (Springer-Verlag,1991).

AMBULATORY PATIENT HEALTH MONITORING TECHNIQUES UTILIZING INTERACTIVE VISUAL COMMUNICATION

CROSS-REFERENCE TO RELATED APPLICATION

This is a continuation-in-part application to application Ser. No. 07/857,470 filed Mar. 25, 1992 now abandoned.

BACKGROUND OF THE INVENTION

A. Field of the Invention

This invention relates to techniques for monitoring the medical condition of a patient, and, more particularly, to a method and apparatus for monitoring a patient at a remote site from a central station by means of interactive visual communications techniques and devices. While the invention is also suitable for use in any situation where a patient is to be monitored at a site remote from a central station, it is especially suitable to the monitoring and caring for the elderly in the home environment. Thus, the invention can also be said to relate to the field of geriatric care.

B. The Prior Art

1. General Considerations

Modern society with its improvement in living conditions and advanced health care has brought about a marked prolongation of life expectancy. This change has resulted in a dramatic and progressive increase in the geriatric population. A large percentage of the geriatric population needs continuous general, as well as medical, supervision and care. For example, supervision of daily activities such as dressing, personal hygiene, eating and safety as well as supervision of their health status is necessary. Furthermore, the relief of loneliness and anxiety is a major, yet unsolved, problem that has to be dealt with. These and other facets of the management of the ever increasing geriatric population have yet to be successfully addressed and solved.

The creation of retirement facilities and old age homes, as well as other geriatric facilities, provide only a partial solution to the problems facing the geriatric population. The geriatric population, a constantly increasing fraction of society, has become increasingly dependent upon the delivery of home health and general care, which has its own set of challenges and drawbacks.

The notion of ambulatory (home environment) patient care is gaining increased popularity and importance. According to some recently published reports, the number of old aged people receiving home care services under Medicare has shown a 13% annual growth rate and has tripled in 10 years (1978–1988) from 769,000 to 2.59 million. This dramatic shift in patient care from the "sheltered" institutional milieu to the patient's home, work place, or recreational environment is due primarily to a radical change in concepts. That is, specialists in geriatric care tend to keep the aged in their own natural environment for as long as possible. Moreover, the marked increase in the cost of institutional patient care, the important technological advances and the development of medical equipment, and the explosive development in the field of telecommunication are some of the additional factors that may help in creating proper home care for the aged.

Presently, geriatric home care is still in its first stages of development. However, according to some recently published market research reports, the market for home care services and products is booming. Annual spending on home care services is expected to increase from $8.8 billion in 1988 to $16 billion in 1995, while annual spending on home care products will increase from $1.15 billion to $1.86 billion during the same period.

Except for scarce model organizations, home care is carried out either by the patient's family or by nonprofessional help. The monitoring equipment at home care facilities is usually minimal or nonexistent, and the patient has to be transported to the doctor's office or other diagnostic facility to allow proper evaluation and treatment.

Patient follow-up is done by means of home visits of nurses which are of sporadic nature, time consuming and generally very expensive. A visiting nurse can perform about 5-6 home visits per day. The visits have to be short and can usually not be carried out on a daily basis. Moreover, a visiting nurse program provides no facilities for continuous monitoring of the patient and thus no care, except in fortuitous circumstances, in times of emergency. The remainder of day after the visiting nurse has left is often a period of isolation and loneliness for the elderly patient.

The existing home care nursing facilities divert skilled nurses, a scarce commodity, from the hospital environment and uses them in a highly inefficient manner due to the wide dispersion of the patients' and the lack of sophisticated diagnostic facilities in the patients home. Clearly, the practice of visiting nurses leaves much to be desired.

These considerations apply to the general population as well, as the spiraling cost of hospital care has lead to a dramatic increase in the use of outpatient care as a treatment modality.

2. Prior Art Models of Ambulatory Patient Monitoring:

One of the areas in which ambulatory patient monitoring is most widely used is out-of-the-hospital surveillance of the cardiac patient. Patients with cardiovascular problems (diseases of the heart and blood vessels) constitute the largest and most important diagnostic and therapeutic challenge facing the authorities responsible for the deployment of health care to the adult and specifically aging population in the U.S. About 15% of the adult population of the industrialized world suffers from hypertension, a major risk factor for atherosclerosis, heart disease, and stroke. Other commonly accepted risk factors such as: elevated blood lipid levels, obesity, diabetes, smoking, mental stress and others are also abundant.

Every year more than 1.5 million people in the U.S. suffer a heart attack. This together with stroke constitutes the number one cause of death in our adult population. More importantly, the majority of cardiac related deaths occur outside of the sophisticated and sheltered hospital environment. Therefore the need for means for ambulatory monitoring of these patients is obvious.

To date the electrocardiogram (ECG) and blood pressure are two main parameters most commonly monitored in the out-of-the-hospital environment. Holter monitoring (continuous 24 hour tape recording of the electrocardiogram) and continuous recording of blood pressure are useful modalities for the evaluation of changes in the cardiovascular system. These, however, are short term monitoring systems that provide only off line information that becomes available at best hours after their recording. Moreover, the hook up should be done by a nurse or technician. Lately, transtelephonic ECG surveillance has been gaining in importance. This system uses small ECG transmitters which allow the transmission of the patients ECG over any telephone line to a diagnostic center. This on-line information system is operative 24 hours a day, 365 days a year. The patient is in direct contact with a highly trained team that can intervene at any time and make real time decisions. The drawback of this system is its communication system, which does not lend itself to prolonged monitoring sessions and does not allow for visual observation of the subject.

A home medical surveillance system is described in U.S. Pat. No. 4,838,275, issued to Lee. This system involves the generation and transmission of health-parameter signals from a patient's home to a central station. However, the described system envisions only two way voice communication between the patient and the observer at the central station. This system does not provide for interactive visual communications between the patient and health care provider, and thus lacks a principal feature and advantage of the present invention.

U.S. Pat. No. 4,524,243 discloses a personal alarm system in which a warning signal is sent to a central monitoring station if the patient's activity level becomes inactive, such as in the case of a medical emergency. This technology is limited in its diagnostic and therapeutic value, and does not, in and of itself, provide for interactive voice or visual communication between the patient and the physician.

Other patents disclose techniques for the transmission of still medical images over a communications line to a remote site. For example, U.S. Pat. No. 4,860,112, issued to Nichols et al., discloses methods and .apparatus for scanning medical images such as x-ray images and transmitting the scanned image to a remote location. U.S. Pat. No. 5,005,126, issued to Haskin, discloses a system for picking off an internal analog video signal from imaging diagnostic equipment such as a CAT scanner and transmitting the image to a remotely located physician's station. U.S. Pat. No. 4,945,410, issued to Walling, discloses a satellite communications system for transmission of still medical images from a remote satellite transmission station to a central headquarters. These patents have their own inherent limitations and lack the interactive audio and visual capabilities provided by the present invention. An ambulatory home care and patient monitoring system, combining a long-term monitoring facility, the possibility of visual contact between the patient and health practitioner, and on-line, real time intervention capability has eluded those in the art.

3. Available Home Health Monitoring Devices:

There exists, at present, home health care and monitoring products that perform various functions. The simplest include, amongst others, instruments such as self-operated blood pressure devices (sphygmomanometers), blood glucose measuring instruments, automated medication dispensers and others. While these products are designed to be useable by a patient without any assistance, they have no inherent capability of remote monitoring. Moreover, they are often difficult to use by elderly or infirm patients.

The other end of the spectrum includes the development of computer controlled robots that provide an integrated, highly sophisticated, home based monitoring unit. An example of such a device is the HANC (Home Automated Nursing Center) system described in U.S. Pat. No. 5,084,828, issued to Kaufman et al. This patent includes a robot capable of monitoring the patient's vital signs, reminding the patient of his or her medications, dispensing them in due time, and contacting a control center for routine follow-up as well as in emergency situations. This device is generally an unsatisfactory solution to the problem of at-home patient monitoring because it is extremely expensive, unfriendly, impersonal, cumbersome, and lacks interactive communication capabilities between the patient and their physician.

The complex robotic units and home computer are impressive in their capacity, but lack the human contact which is so important in effective geriatric care. The patient's interaction with a machine, as sophisticated as it may be, will always be inferior to the direct human contact. Moreover, these systems are very expensive and will in the foreseeable future be available to only a very small number of patients who can afford them. Moreover, the older population does not adjust easily to computers and robots, and mistakes in their use are frequent. Maintenance and problems and the difficulty in programs in the computerized system make the upkeep more complex. Thus, the currently available techniques for providing home patient monitoring, particularly of the elderly, leave much to be desired.

4. Other Geriatric Health Risks

Additional facts support development of an improved home health care system especially for a geriatric population. For example, falls are a major health problem among the elderly, causing injury, disability and death. One third (some studies suggest half) of those over the age of 65 suffer at least one fall each year. The rate of falling increases to 40% among those who exceed the age of 80. According to the National Safety Council, falls accounted for one-third of the death total for the elderly. Those who survive falls may have restricted activity, soft-tissue injuries,, or fractures. It is estimated that up to 5% of falls by elderly persons result in fractures. A similar percent result in soft-tissue injury requiring hospitalization or immobilization for an extended period. It is estimated that hip fractures resulting from falls cost approximately $2 billion in the United States during 1980. Falls are mentioned as a contributing factor to admissions to nursing homes.

The factors leading to falls can be divided into two main groups: environmental factors and medical factors. In spite of the difficulty in the surveillance of patient condition before a fall, almost all researchers share the conclusion that environmental hazards are decreasingly important in causing falls as age increases. A clear correlation between clinical or medical problems and the incident of falls by the elderly has been established. Many of these medical problems of the elderly or infirm can be detected by simple clinical observation. For example gait and balance abnormality may indicate difficulty with neurologic and musculoskeletal functions that may contribute to physical instability. Changes in gait can be identified by the following: slow speed, short step length, narrow stride width, wide range of stepping frequency, a large variability of step length, and increasing variability with increasing frequency.

Thus, there are relatively straight forward techniques which enable diagnosis of a predisposition or likelihood of falls among elderly. However, there is no inexpensive procedure for undertaking such diagnosis or investigating such predisposition in a large patient population wherein the kinematic condition of the patient can be investigated or where the appearance and reflex activity of the patient can be investigated with ease.

SUMMARY OF THE INVENTION

In a principal aspect, the present invention comprises an interactive television and audio patient monitoring system connecting a patient situated at home with a central monitoring station manned by health practitioners (e.g., trained nurses or clinicians). The term "patient" as used herein is to be interpreted broadly to include elderly persons, persons actively being treated or monitored for specific medical ailments, as well as persons who wish to have their general medical condition monitored by health practitioners.

The present invention provides two-way interactive visual communications between the patient and the central station. The invention also provides for the monitoring by the central station of any of a number of possible vital signs and diagnostic test data. By way of example and not limitation, the vital signs to be monitored may include blood pressure, temperature, weight, heart rate, respiratory rate, oximetry and so on. At the present, two-way interactive cable television, with its widespread network, provides a two-way communication network suitable for use in the present invention. Its interactive nature provides the personal, visual contact between the patient and the staff located at the monitoring center. Moreover, this communication system provides almost unlimited monitoring time. These attributes enable the collection of a multitude of medical data for prolonged periods of time, as well as the human contact that constitutes an important factor in the care of the population in need for such services. The long-term storage of medical and visual information helps in diagnosis and treatment. The transmission of the visual information and the monitored medical data between the central station and the patient's home may be made by satellite, radio transmission or through telephone lines, instead of cable television lines.

The preferred embodiment of the present invention involves an interactive system for monitoring a patient's condition by health practitioner. The patient is located at a remote location from a central monitoring station and the health practitioner is located at a central station. The system comprises in combination a first audio-visual camera for generating a first audio-visual signal of a patient at the remote location. The system also includes a means for measuring a medical condition of a patient at the remote location and for generating a signal representative of the measured medical condition. The measured medical condition may be any health parameter, such as heart rate, respiratory rate, pulse oximetry, blood pressure, and so on, and will of course vary from patient to patient. A communications network is used for transmission of the first audio-visual signal to the central monitoring station. The medical signal is transmitted simultaneously with the first audio-visual signal. The central station includes a display for substantially simultaneous display of the first audio-visual signal and the medical signal. The system further includes a second audio-visual means for generating a second audio-visual signal of the health practitioner originating from the central station, and the transmission of the second audio-visual signal to the remote location. The system further includes a means for display of the second audio-visual signal at the remote location for observation by the patient preferably simultaneously with the transmission of the first audio-visual transmission, whereby the patient and the health practitioner are capable of substantially simultaneous interactive audio-visual communication concerning the measured medical condition. Typically, the display of the second audio-visual signal at the remote location will be made on a TV set at the patient's home. Preferably, the means for generating the first and second audio-visual signals are conventional cameras such as camcorder type cameras. Thus, the present invention is readily adaptable to existing technology and can be implemented at relatively low cost.

The new, integrative, highly sophisticated and cost-effective home monitoring system combining modern sensors and measuring devices with interactive television solves many of the problems facing an ever growing fraction of society. The geriatric population, the chronically ill, the handicapped, and patients discharged from hospitals but still in need of monitoring are only some examples of those who benefit from the invention.

As a further aspect of the invention, the visual signal generated by the audio visual means associated with the patient may be relied upon to measure the medical condition of the patient directly. That is, patient gait, mobility, appearance and other visual aspects of a patient, which may be relied upon by medical practitioners to evaluate the patient, may be designated, marked, specified or tagged electronically in the visual signal from the patient and thereby serve as a time dependent measurement of the medical condition of the patient. Such measurements are transmitted to the central station and processed electronically or visually. Electronically the information may be stored or compared to standard data or previously stored base line data associated with the patient. This technique may be conducted utilizing analytical softwear or by a trained technician or physician. Diagnosis of a propensity to fall may, for example, be derived. Other diagnosis may also be derived in this manner.

Thus, an objective of this invention is to provide a central, remote home care surveillance system combining a relatively inexpensive patient monitoring devices with a sophisticated central surveillance center using available telecommunication systems. The present invention provides an interactive and cost-effective system that will allow around-the-clock supervision of the various aspects of the patient's daily activities and health in the home environment.

Moreover, the invention provides the capability for a physician at a remote location, such as the physician's office, to interact audially and visually with the patient.

A further object is to provide, an efficient and economical health care system. Ambulatory patient care is by far more economical than institutional care. More importantly, it allows diagnostic and therapeutic assessments in the patient's natural environmental rather than in the "sterile" setting of a hospital ward. The equipment involved is easy to use and alleviates the problem of frequent mistakes common in other systems. Some of the benefits of audio-visual interactive communication features of the present invention include: 1) enhancement of diagnosis by the physician; 2) facilitation of instruction of the patient in the use of home-based medical equipment and the administration of medicines, as well as avoidance of mistake or misuse; 3) observation of the patient in times of medical emergency, particularly if the patient cannot speak; 4) psychological benefits by having a nurse "visit" the patient electronically, and the comfort of knowing that the patient can have this "visit" any time a problem occurs; and 5) facilitation of group instruction of a large number of patients at the same time. Group instruction in, for example, preventative medicine or general health matters can take place with the patients being capable of asking questions.

These and other advantages and features of the subject invention will become apparent from the detailed description of preferred and alternative embodiments which follows.

BRIEF DESCRIPTION OF THE DRAWING

In the detailed description of presently preferred embodiments of the present invention which follows, reference will be made to the drawings comprised of the following figures, wherein like reference numerals refer to like elements in the various views and wherein.

DESCRIPTION OF THE PREFERRED EMBODIMENT

Figure 1:
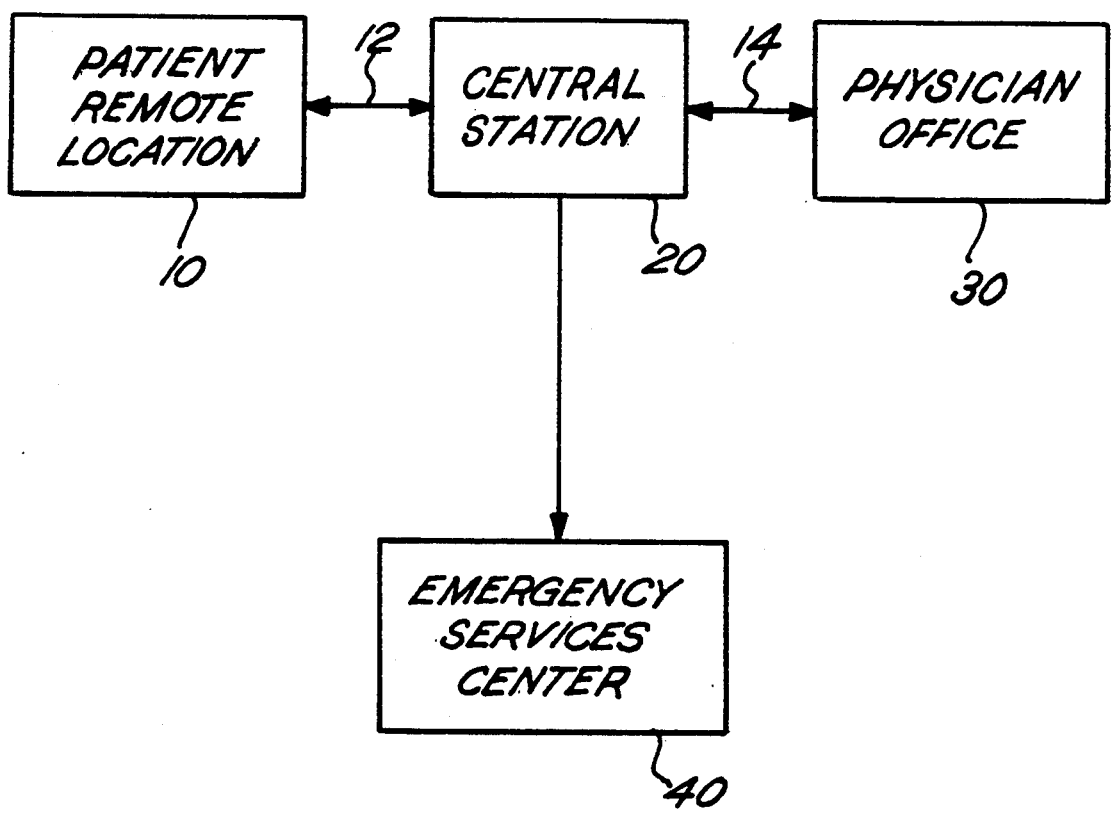
FIG. 1 is a simplified, overall functional block diagram of the health monitoring system of the present invention.

Briefly, a method and apparatus are provided for monitoring a medical condition of a patient by means of instrumentation maintained at the patient's living quarters linked through a communications network to a central surveillance station. The system is interactive since the patient and personnel at the central station may engage in two-way audio and visual communication.

General Description:

The system uses or incorporates inexpensive home medical monitoring equipment that includes sensors and measuring devices for the particular medical parameters to be monitored. The patient's home equipment is simple to use and modular to allow for the accommodation of the monitoring device to the specific needs of each patient. To reduce production costs and to avoid complex maintenance problems, the home unit includes only the sensor part of the measuring device. The raw data is transmitted to the central station, which includes all of the needed sophistication to allow for the storage, transformation, display and interpretation of the data. The need for expensive equipment in the home is thus avoided. Inexpensive sensors are placed in the patients' homes, and the more costly analytic equipment for all the patients is located at the central station.

The central station includes a computer-based multi-channel data analysis and display unit that enables the interpretation, display, and storage of the transmitted data. This central station is preferably equipped with alarm mechanisms to alert the staff to any aberration from the expected. The central station further includes apparatus for the communication of data to all authorities involved in the wide spectrum of the patient's needs, e.g., emergency care agencies, the patient's physician, nursing services, social workers, etc.

The central station is preferably provided with the capability of automatically scanning predesignated patient home units at predetermined intervals to provide continuous supervision of specific parameters. In some instances, the central station may monitor continuously one or more parameters, e.g., ECG, blood pressure, respiration, etc., for hours or even days, thereby creating a semi-intensive-care capability. The embodiment disclosed enables one highly trained nurse or patient monitoring personnel located at the control center to supervise and monitor as many as 50 patients either seriatim or substantially simultaneously. Whereas a visiting nurse may only be able to visit 5 or 6 homes per day in person, a nurse at the central station may be able to visit 5 or 6 patients per hour by making electronic "home visits".

Cable television provides an already existing, widespread and ideal system for interactive visual communication with most residential units in densely populated urban areas. The ambulatory patient monitoring system integrating the latest advances in biomedical technology with cable television provide safe and accurate general and medical supervision for the geriatric/homebound population in their own, natural environment.

Using such an interactive system, a direct visual uni- or bi-directional contact between the elderly person monitored and the supervision is established at any time, day or night. This contact can be initiated, at will, by the patient monitor or by the patient. Moreover, this communication system is used to transfer general data as well as medical data from sensors to monitor the various medical and non-medical parameters. Further, a health practitioner may be able to have "classes" with many remotely located patients.

Cable television networks provide a useful mode of communication between the patient's remote location and the central station at the present, and is a presently preferred means for transmission of the audio-visual signal from the patient to the central station and for transmission of the audio-visual signal of a health practitioner to the patient's remote location. Further, the measured medical data can be displayed in the patient's remote location and the parameters picked up by the camera. The transmission of the measured medical data may also be by cable television, or may be through another communication network such as the telephone system. The data transmission could also be by microwave, cable, or other transmission means. It will be appreciated that as advances in telecommunications develop, other techniques for transmission of video signals between a central station and the home may be desirable and economically feasible. For example, satellite and radio transmission of the video signal and/or monitored medical data, or transmission via modem through the telephone lines, may also prove satisfactory.

Communication between the patient's remote location and the central station can be initiated by a variety of techniques. One method is by manually or automatically placing a call on the telephone to the patient's home or to the central station. When the call is received, a responsive switch is thrown, turning on the camera in the patient's home or at the central station. Alternatively, the patient and central station could agree on times or time intervals in which communication would take place. Ideally, a remote control button 220 on the patient's chair (FIG. 10) is installed which, when activated, turns on the equipment in the home and alerts the health practitioner at the central station.

Referring now to FIG. 1, a greatly simplified schematic diagram of the ambulatory patient monitoring invention is shown. Ambulatory patients located in a remote location 10, such as the home, are monitored from a central surveillance station 20. Only one remote location 10 is shown, for the sake of simplicity. Audio and visual signals of the patient, as well as medical data measured in the home such as heart rate, blood pressure, temperature, oximetry data, etc., are sent over a communications network 12 to the central station 20. The audio-visual information and the measured medical data are displayed at the central station 20 on display equipment such as television monitors. The audio-visual information of the patient, as well as the medical data, is monitored by a health care worker such as a nurse at the central station 20. The system of FIG. 1 also includes the generation of a second audio-visual signal of the health care practitioner at the central station 20 and the transmission of the audio-visual signal over a communications network 12 to the patient's home or remote location 10. The second audio-visual signal is displayed in the patient's remote location 10 on a television set. The transmission of the second audio-visual signal of the health practitioner to the patient's remote location 10 is preferably substantially simultaneous with the incoming audio-visual signal from the patient and permits the patient and health practitioner to engage in interactive visual communication concerning the patient's current medical condition. The term "substantially simultaneous" is meant to include actual simultaneous transfer, as well as the situation where the patient and central station transmissions are separated in time but immediately follow each other, as may be required by equipment limitations in some cable television systems.

The system of FIG. 1 also includes the capability of a physician at a remote location 30 to engage in interactive visual communication with the patient. At location 30, the physician may gain access by a second communications network 14 to access the patient's health data or audio-visual signal at the central surveillance station 20. Also, the invention provides the capability of the patient gaining access to an audio-visual signal of the physician.

Should the patient be experiencing health symptoms requiring intervention and immediate care, the health care practitioner at the central station 20 may summon help from an emergency services provider 40. The emergency services provider may send an ambulance, fire department personnel, family member, or other emergency personnel to the patient's remote location 10. The emergency services provider 40 may, perhaps, be an ambulance facility, a police station, the local fire department, or any suitable support facility.

Figure 2:
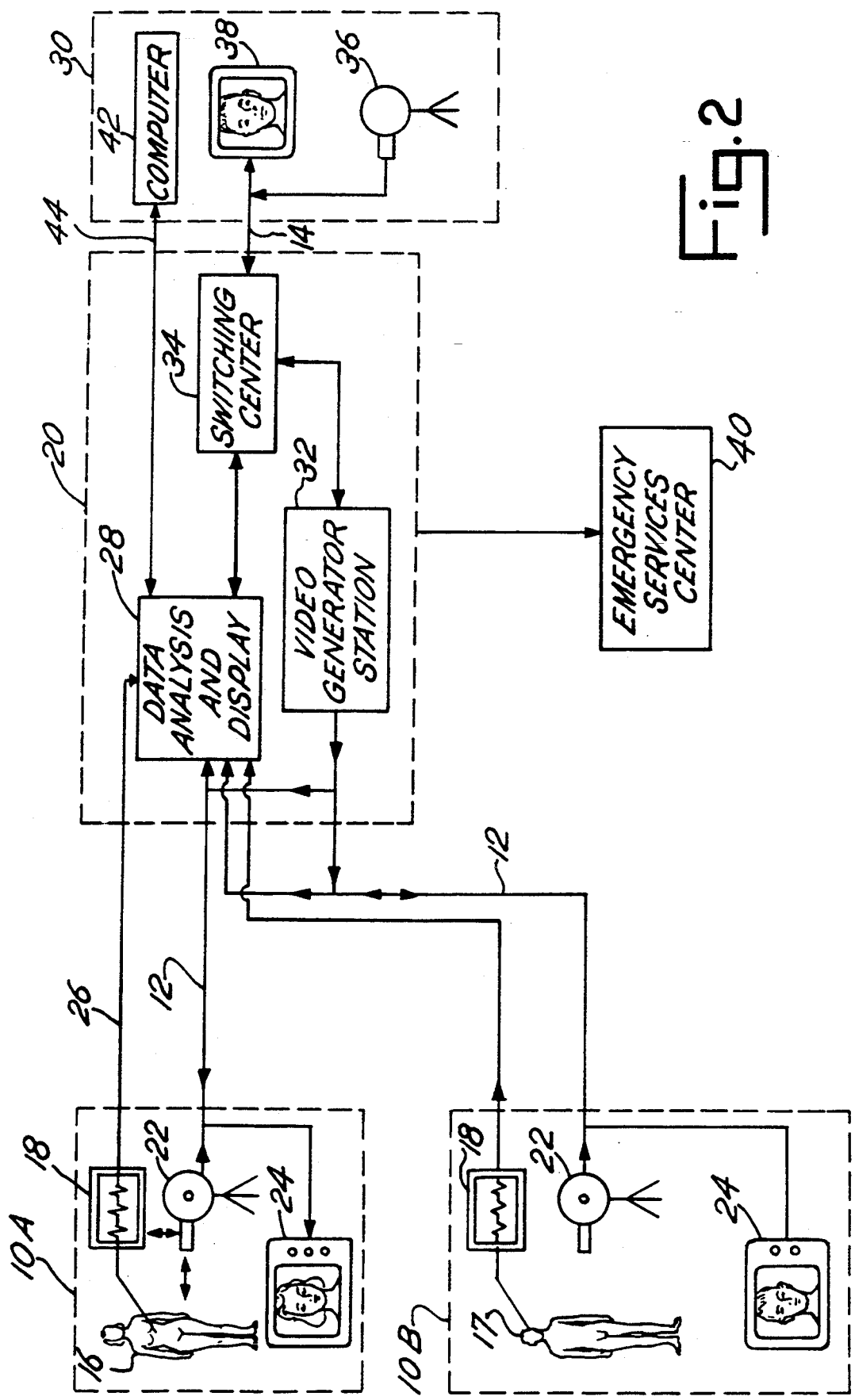
FIG. 2 is a more detailed functional block diagram of the system of FIG. 1, showing a central station simultaneously monitoring a plurality of patients in remote locations.

Referring now to FIG. 2, the ambulatory patient health monitoring invention is shown in a more detailed functional block diagram. The present invention provides for the capability of a health care practitioner at the central station 20 to monitor any given number of patients at remote sites. FIG. 2 shows remote sites 10A and 10B, but of course there may be any number of subscriber patients which may be monitored by the central station 20 and only two are shown for purposes of simplicity. At the remote site 10A, the patient 16 has in the home sensing equipment 18 for measurement of a medical condition of the patient 16, such as a blood pressure gauge, a comprehensive non-invasive patient monitor device such as the Criticare Systems, Inc. Model 507 monitor, a simple thermometer, oximetry equipment, or other equipment depending on the patient's medical status. Preferably, the sensing equipment 18 requires passive or only minimal activity on the part of the patient. The patient 16 also has in his home 10A a camera 22 suitable for generating an audio-visual signal of the patient 16. The patient 16 also has in his home 10A a television set 24 or other suitable means for displaying a audio-visual image of a health care practitioner located at the central station 20.

Special equipment may be used for measuring medical parameters of the patient with only minimal involvement by the patient. For example, a chair (not shown) may be provided which includes sensors for measuring the patient's temperature and weight, a blood-pressure cuff for measuring the patient's blood pressure, electrodes for monitoring the patient's ECG, and sensors for measuring the patient's pulse. Preferably, most of these sensors are placed directly on the arms of the chair so that the patient's medical data can be derived with minimal participation by the patient. The sensors can be wired directly to a signal conditioning and transmission unit (not shown) for amplification, analog to digital conversion, data storage and transmission to the central station 20 over the telephone line. A preferred modular medical condition sensing and display unit is discussed below in conjunction with FIG. 10.

In operation, the health monitoring and sensing equipment 18 measures the medical condition of the patient and generate, s a signal representative of the measured medical condition, and transmits the raw data directly to the central station over a transmission line 26 such as the telephone, or perhaps sends it by a radio frequency transmitter to the central station 20. The data can also be sent directly over the cable television line to the central station. Techniques for transmission of medical information over a transmission line such as a telephone line are well known in the art. Alternatively, the camera 22 may have its lens focused on the display of the health monitor equipment 18, such as the face of the Criticare Systems monitor, or the dial of a blood pressure gauge, or the face of digital thermometer. The camera 22 also is used to generate an audio-visual signal of the patient 16. The audio-visual signal generated by the camera 22 is then transmitted over the communications network 12 to the central station 20. The communications network 12 can be a cable television cable provided by a cable company to the patient's location 10A (discussed in detail below), or may be a telephone line through which the digitized audio-visual signal is transmitted from the patient 16 to the central station 20. Alternatively, the communications network may be any other suitable transmission network or means for transmitting the audio-visual signals to the central station, such as satellite transmission. The TV set 24 serves as a means for displaying in the patient's location 10A the audio-visual signal of the health practitioner at the central station that is interacting with the patient in the home. In its simplest form, the invention can be practiced by transmitting the measurements of the patient's medical condition to the central station 20 by using the camera 22 to record the displays of the sensing equipment 18. However, better use and analysis of the measured medical data may be afforded if the medical data is transmitted over a separate communications line 26. However, the data transmission does not have to be a separate line, as the signals can be superimposed on each other. For example, the output from the sensors can be transmitted through the audio channel together with speech.

The equipment used at a second remote site 10B is essentially the same as 10A. Of course, it will be appreciated that the patient 17 at location 10B may have an entirely different set of medical conditions to be monitored, and thus the medical condition measuring and sensing equipment 18 at location 10B may be entirely different than the equipment 18 at location 10A.

The central station 20 includes a data analysis and display center 28, an audio-visual signal generation station 32 and a switching center 34. The data analysis and display center 28 receives the incoming data transmitted by the health monitoring equipment 18 at the patient's remote location. The data analysis and display station 28 also receives the incoming audio-visual signals from the patients' cameras 22. The data analysis and display station 28 includes equipment to process the health monitoring data, and to store and retrieve the data. The data, including the audio-visual signal of the patient 16, is retrieved and displayed as desired by the health practitioner. For example, the health practitioner at the central station 20 may wish to see the image of the patient generated by the camera 22, or may wish to generate graphs or ECG maps of cardiac activity, or review the history of the patient's heart rate over the previous 24-hour period. These are just a few illustrative examples of the use that can be made out of the transmitted medical information. The central station 20 is also provided with a set of the patients' medical records in order to compare the incoming medical data and audio-visual signal with the patients' history. If alarm conditions are present, suitable action can be taken by the health practitioner.

The video generation station 32 includes at least one video camera (not shown) for generating an audio-visual signal of a health practitioner and transmission equipment to transmit the signal to the patients 16, 17 at the remote sites 10A and 10B. The patient can therefore see the face of a health care worker and interact in an audio-visual manner with the health practitioner concerning his or her medical condition. If a staff or team of patient monitors or health care workers at the central station are employed, as when a large number of patients are being monitored, multiple cameras or even small-scale studios may be used, one for each health monitor or nurse, so that individual patients at the remote locations can see their own particular health care worker that they are used to.

The switching center 34 serves to direct the incoming and outgoing signals from the patients and the health care workers at the central station 20 to orchestrate the proper channeling of the incoming and outgoing audio-visual signals. The switching center 34 further has the capability of permitting access by a physician at a remote site 30 to the medical data or audio-visual signal of the patient 16.

The remote site 30, which may be the physician's office, his home, or a hospital at a remote location, includes a camera 36 for generating an audio-visual signal of the physician at the remote site 30. The audio-visual signal of the physician is sent over a communications line 14 (such as cable television lines) to the switching center 34 and sent out to the patients' remote locations 10A and 10B, thus permitting the physician to interact in an audio-visual manner with the patients. The remote site 30 also has a monitor 38 (such as the television set) for display of the audio-visual signal of the patient 16. The physician at the remote site 30 may also have a personal computer 42 to gain access via a modem (not shown) and a telephone line 44 to the patient's medical information stored in the data analysis and display unit 28 in the central station 20.

If the health practitioner at the central station 20, or the physician at the remote site 30, determine from the medical data that the patient 16 is in need of emergency treatment, the physician at the remote site 30 or the health practitioner at the central station 20 may put in a phone call to the emergency services provider 40 and direct personnel at that location to send immediate help to the patient 16. For example, if the patient 16 at home undergoes a cardiac arrest, and the transmitted audio-visual or medical signals reflect this condition, the health practitioner at the central station 20, can immediately summon help. The data analysis and display unit 28 of the central station may also incorporate routines for automatically alerting the emergency services provider 40 when the measured medical condition of the patient reaches a predetermined threshold. Medical alarm systems are also known in the art, such as U.S. Pat. No. 4,524,243, which is incorporated by reference herein.

Figure 3:
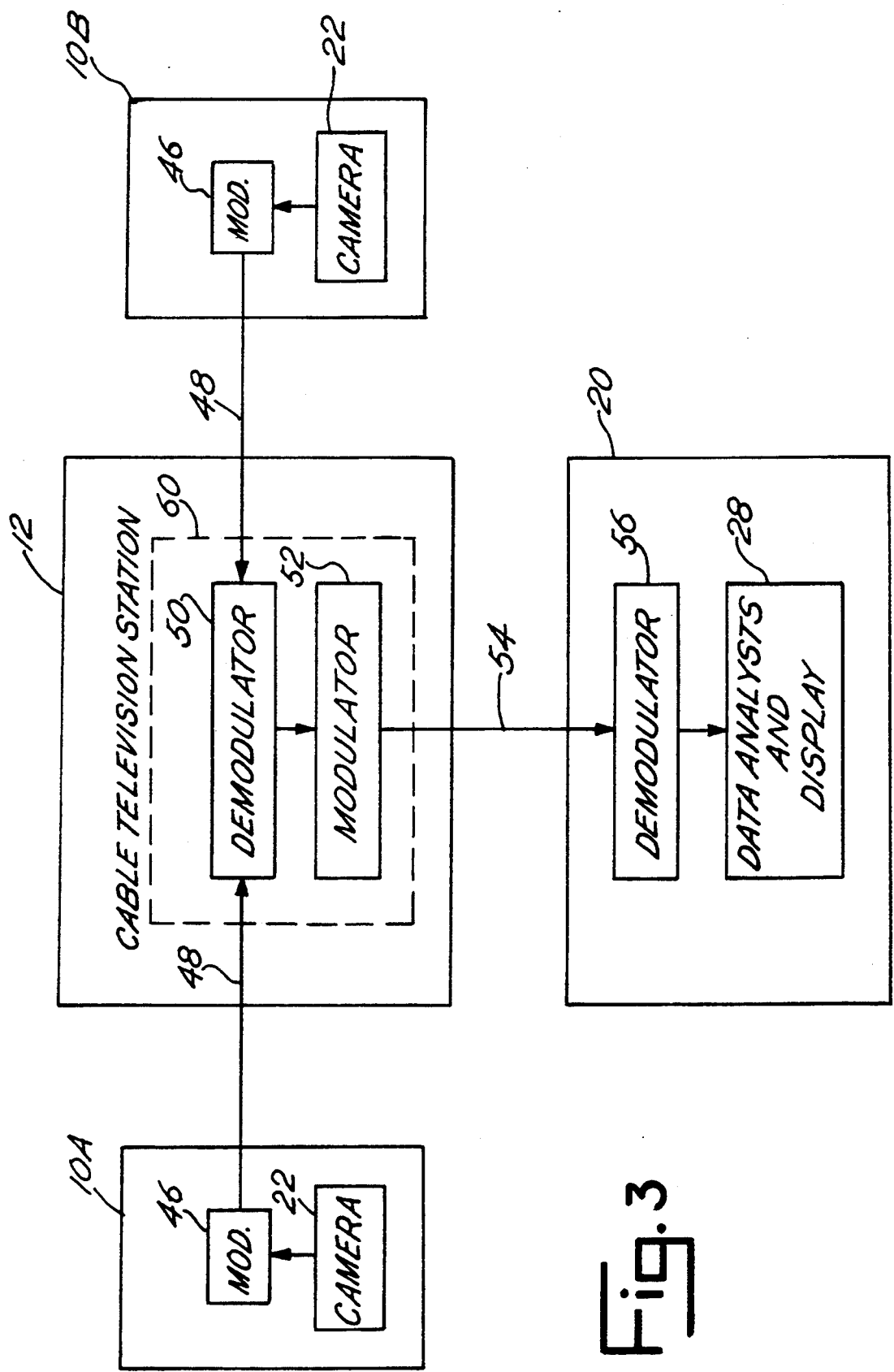
FIG. 3 is a schematic diagram illustrating how an audio-visual signal of a patient may be transmitted via cable television lines from a patient's remote location to the central station of FIG. 1.

Referring now to FIG. 3, a schematic diagram of the communications network 12 for transmitting an audio-visual signal from the patient's home to the central station using cable television lines is illustrated. In the patients' homes 10A and 10B, there is a camera 22 which generates an audio-visual signal of the patient and/or display screen of health monitoring equipment and transmits the signal to a modulator 46. The modulator 46 converts the audio-visual signal into a high-frequency (5–30 MHz) signal which is sent from the modulator 46 through the cable line 48 to the local cable television station 60. The signal on cable line 48 is sent to a demodulator 50 in the cable television station 60 which regenerates the audio-visual signal, and then the audio-visual signal is sent to another modulator 52, which sends the audio-visual signals from the homes 10A and 10B through another cable line 54 to the central station 20. The modulated signal on cable television line 54 is demodulated in a demodulator unit 56 and then stored and displayed in the data analysis and display unit 28 in the central surveillance station 20. Those of ordinary skill in the cable television transmission art are familiar with the modulator and demodulator units shown in FIG. 3. Background information on cable television transmission is contained in G. Fink and D. Christiansen, *Electronics Engineers' Handbook*, McGraw-Hill, Sections 21-73 through 21-86 (3rd ed. 1989), which is incorporated by reference herein.

Figure 4:
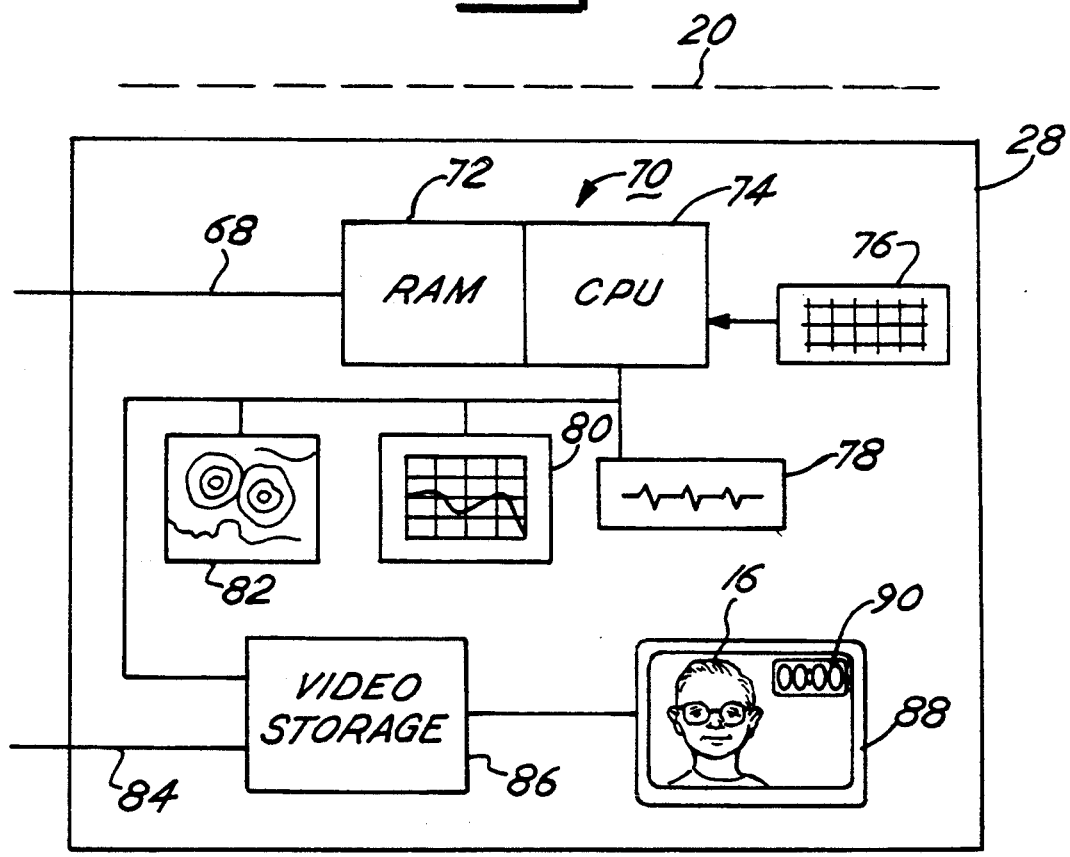
FIG. 4 is a more detailed functional block diagram of the data analysis and display center of the central station of FIG. 2.

Referring now to FIG. 4, the data analysis and display unit 28 of FIG. 2 is shown in more detail. Data indicating the medical condition of the patient is sensed in the patients' remote location and may be sent via the telephone lines to the central station 20. The data is in turn relayed on a data bus 68 into a central computer 70. The central computer 70 has both a data storage center 72 (including a random access memory and a series of hard disk drives or magnetic tape drives), and a central processing unit (CPU) 74. The data storage center 72 stores incoming patient data for a given period of time, which may be over 24 hours, so that a physician or health practitioner can go back through the patient's medical data, during the previous 24 hours for example, and ascertain what the patient's health or condition was at a certain period of time. This capability is important for diagnostic purposes because it allows the physician to monitor and analyze the patient's medical condition prior to a given event such as a cardiac arrest. The physician can simply enter commands into the keyboard 76 to access particular data from a particular period of time and display the information.

For example, the physician may have the patient monitored for electrical activity in the heart. The patient will have a set of electrodes attached to his chest and the electrical potentials are measured on the surface of the chest. The data is sent over the communications network 12 (FIG. 1) to the central station 20 and stored in the central computer 70. The information from the patient may be displayed in the form of an electrocardiogram 78, or the patient's blood pressure may be plotted as a function of time in a graphical form on a computer screen 80. Alternatively, a two-dimensional map of the electrical activity in the patient's heart may be displayed on a special display monitor 82 for that purpose. The generation of images of electrical activity in the body is well-known in the art. One article discussing this technology is Perrin et al., *Scalp Current Density Mapping: Value and Estimation from Potential Data*, IEEE Transactions on Biomedical Engineering, Vol. 34, Page 283-288 (1987), which is incorporated by reference herein. The diagnostic capabilities are especially enhanced if the patient has a dedicated line from the remote location 10 to the central station 20 (FIG. 1) for continuous transmission of medical data to the central station. The data analysis and display unit 28 may further include a means for transferring the medical data onto high storage capacity media such as optical disks, which can then be retrieved at a later point in time. The diagnostic tools provided by this data analysis and display center significantly enhances the ability to monitor patients in the home and to diagnose precise medical conditions based on the collected data.

Alternatively, the measured medical data may be stored in the patient's home for relatively long-term periods (e.g. 24 hours) and then transmitted all at once to the central station. An example of equipment suitable for this purpose is discussed below in conjunction with FIGS. 7-9.

Still referring to FIG. 4, the audio-visual signal from the patient is fed on cable 84 to a video storage unit 86. Again, a physician may enter commands at the keyboard 76 for the central computer 70 and retrieve the audio-visual signal stored in the video storage unit 86 such that he or she can see the picture of the patient on a TV screen 88 either simultaneous with its transmission from the patients' remote location 10, or during a previous period of time. For example, if the patient was experiencing chest pains at 3:00 a.m. the previous day, the physician may want to see the picture of the patient at 3:00 a.m. The physician enters a command into the keyboard 76, or manipulates the video data storage device 86, such as a VCR, to retrieve the video picture of the patient 16 at 3:00 a.m. The picture of the patient 16 is displayed on the screen 88 together with a time field 90. The physician can then have the display units 82 or 78 display the electrocardiograms in a one or two-dimensional image to correspond with the patient's picture at that period of time so he can match up the medical data with the video image of the patient.

Figure 5:
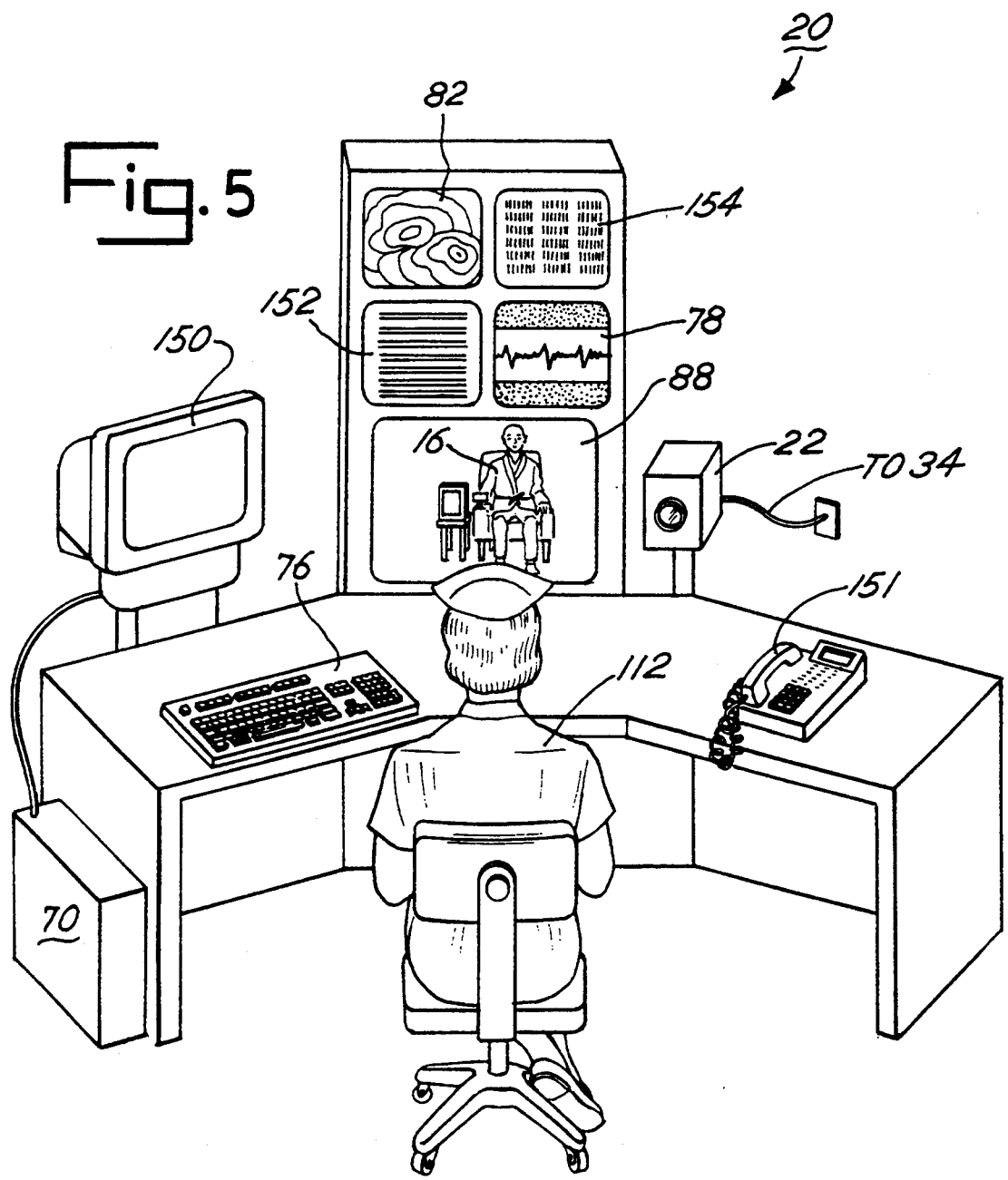
FIG. 5 is an illustration of one possible arrangement of the health monitoring and telecommunications equipment in the central stations.

Referring now to FIG. 5, there is illustrated one possible arrangement of the health monitoring and telecommunications equipment at the central station 20 surrounding the health practitioner or nurse 112. The nurse 112 enters via keyboard 76 of the central computer 70 commands to call up on the TV screen 88 the patient 16 of interest. The commands may also include commands to start up the camera in the patients home. The central computer 70 is linked with the switching center 34 (FIG. 2) such that any of the subscriber patients can be accessed. Preferably, the patient's medical records and history are entered into the computer 22 such that when the particular patient is selected, the history is displayed either on the display 150 of computer 70 or on a separate screen 152. This enables the nurse 112 to rapidly familiarize herself with the patient. If the patient's data is being simultaneously transmitted to the central station 20, the patient's ECG or cardiac activity can be displayed on displays 78 and 82, respectively. Alternatively, the patient's oximetry data may be displayed for a given period of time on a separate display 154.

The nurse 112 also has a camera 22 oriented towards her which generates an audio-visual signal for transmission to the patient's remote location 10. If a cable television communications network is used, the signal generated by camera 22 will typically be sent to a modulator unit (not shown) and then to the local cable television station for ultimate transmission to the patient's home. The nurse 112 will preferably also have a telephone 151 nearby for telephoning the emergency services provider 40 (FIG. 1) if the patient 16 should need immediate care.

Figure 6:
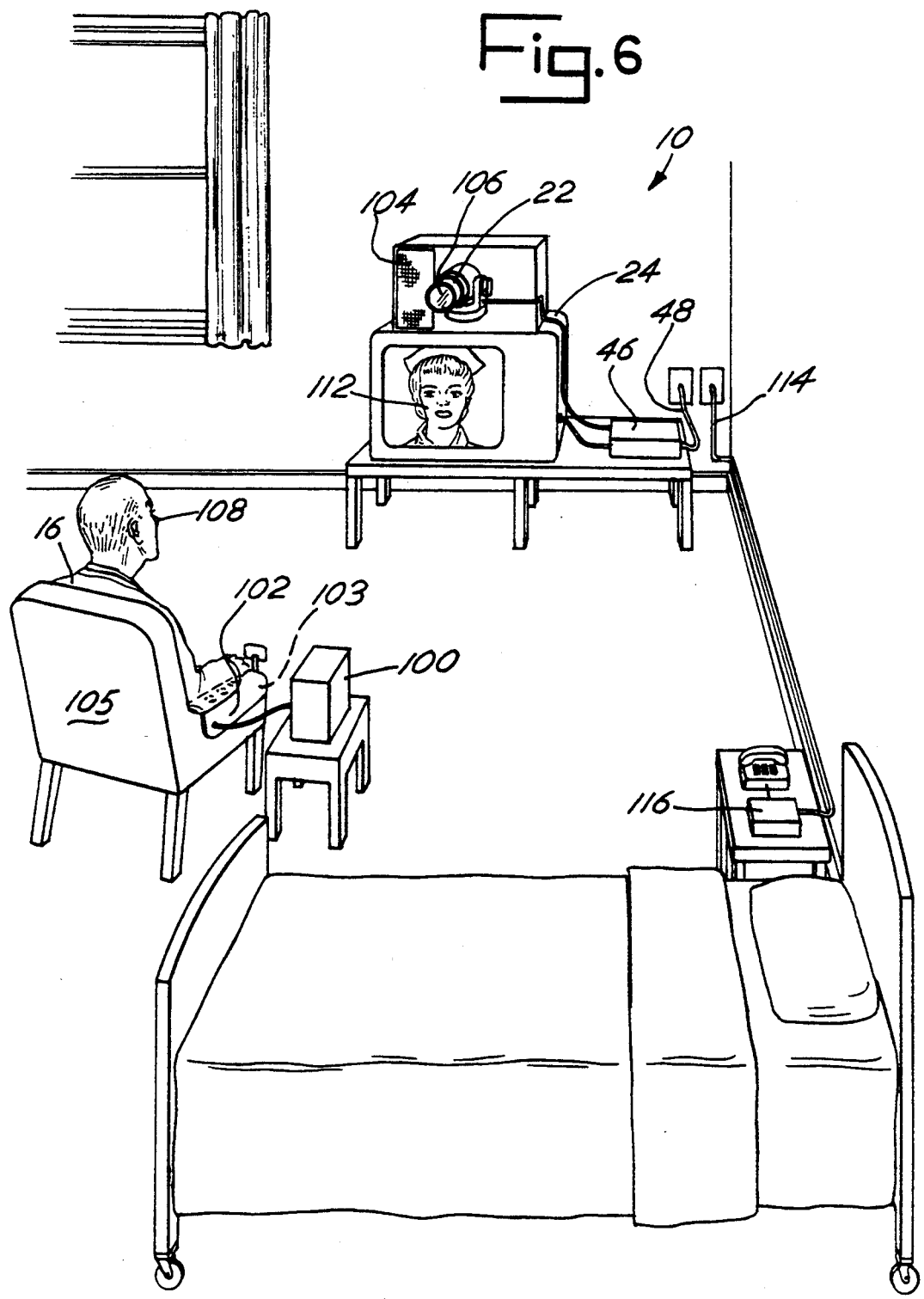
FIG. 6 is an illustration of one possible arrangement of the medical condition measuring, sensing and telecommunications equipment in a patient's home environment.
Figure 10:
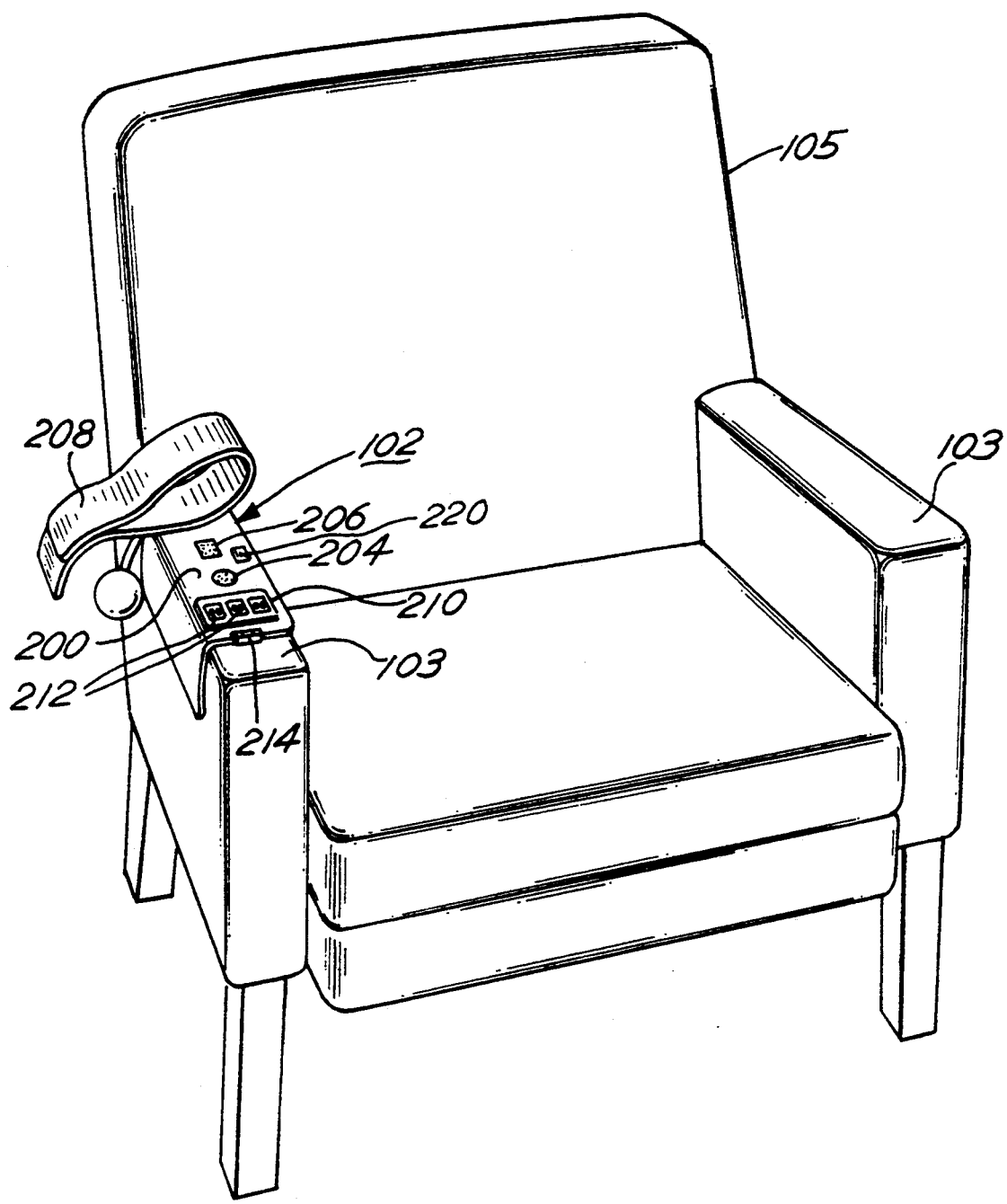
FIG. 10 is a more detailed illustration of the modular medical condition sensing and display unit of FIG. 6 which may be used in the patient's home environment.

Referring now to FIG. 6, there is illustrated one example of the equipment which may be used in monitoring the medical condition of a patient in a home environment. The patient 16 may have in his home 10 a variety of equipment for measuring the medical condition of the patient and the present example shown in FIG. 6 is for purposes of illustration, and not limitation. The patient 16 in this example has a Criticare monitor unit 100 to which patient 16 is hooked up and the Criticare monitor 100 measures the pulse rate, blood pressure, oximetry, and temperature of the patient and displays the information on the screen of the monitor unit 100. The patient may alternatively have a modular medical sensing and display unit 102 resting on the arm 103 of the chair 105. This unit 102 is discussed in detail below. The patient may also have a set of electrodes (not shown in FIG. 6) attached to his or her chest for use in generating electrocardiograms. In the patient's home 10, a conventional video camera 22 such as a videocassette camcorder-type camera is mounted in a cabinet 104 a short distance away from the patient. The camera 22 includes a lens 106 oriented in the direction of the patient 16. The patient is seated in the chair 105 a sufficient distance away from the camera 22 such that the field of view of the camera 22 includes the entire patient's body, as well as the screen of the Criticare monitor 100 or the display 210 of the unit 102 (FIG. 10). The video camera 22 then films the patient or the screen of the patient monitoring equipment and transmits the audio-visual signal via the modulator 46 through the cable TV line 48 from the home 10 to the cable television station 60 (FIG. 3). Suitable servomotors (not shown) are provided within the cabinet 104 such that the camera focus and orientation can be controlled by the monitoring health practitioner at the central station. The camera 22 may also include start up controls which can be remotely operated by the health practitioner to enable the health practitioner to initiate patient monitoring via camera 22.

The patient 16 in his home 10 substantially simultaneously receives an audio-visual signal from the health practitioner 112 at the central station that is monitoring the transmitted signals from the patient's home 10. The health practitioner 112 is able to interact visually with the patient 16 as the camera 22 is filming the patient 16 and/or the Criticare monitor 100 or unit 102. For example, the health practitioner 112 can inquire as to how the patient 16 is feeling, and if the patient 16 complains of chest pains, the health practitioner 112 can see the face of the Criticare monitor or the display 210 of the unit 102 (FIG. 10) to observe the current data.

Of course, if the medical data is being transmitted simultaneously via the telephone line 114 or digitally through the cable line 48, then the health practitioner 112 can have the information displayed at the central station. The displays of the Criticare monitor 100 and unit 102 are, in this scenario, redundant. However, they serve as useful backups if the digital transmission is interrupted or fails.

The patient depicted in FIG. 6 may also be examined for various ambulatory and other physical characteristics useful in the diagnosis of patient health, for example the predisposition to fall. For example, gait and mobility of the patient may be examined and analyzed using the system of the invention. Specifically, the video camera 22 may include a lens having a wide angle. The patient 16 can be orally instructed by the health practitioner to position himself at a start position in the vision field, for example, standing erect at the center of the visual field at a specified distance from the camera 22. The patient will have attached reflective strips of tape to various designated locations on his body. For example, reflective tape may be placed on the wrists, elbows, shoulders, etc. Alternatively, the patient can put on a pre-sized shirt or jacket with the reflective strips or markers preattached thereto. Similarly, trousers with such reflective strips or markers may be put on by the patient.

The reflective strips act as markers used in the subsequent diagnostic activities. Thus, the practioner 112 will direct the patient 12, having been positioned at a start position with markers locating specific body parts, to conduct specific physical activities such as specific arm movements, walking, bending, etc.

The visual signals associated with the marker positions as transmitted to the central station can be recorded. Further, the specific markers can be electronically tagged for analysis. Thus, the markers will create a record of specific body part movement for comparison electronically to previously stored standard data or previously recorded data for that patient. Also the recorded visual signal may be reviewed by the practioner for purposes of diagnosis and advice to the patient. Thus, the predisposition of a patient to fall and the potential reasons for a fall can be predicted and preventive intervention can be attempted. For example, a change in medication can be prescribed or physical therapy may be instituted. The system may then be utilized to monitor the results of the prescribed medication or therapy.

A video/computer motion measurement system that may be useful in the conduct of such diagnostic and analytical practice is made by Peak Performance Technologies Inc., Englewood, Colo. and is identified as the Peak 2D system and the Peak 5 system. Other video motion analytical systems may be utilized in combination with the system of the invention. Additionally, numerous other types of measurement and diagnoses may be performed utilizing the video signals derived from the patient. Such diagnoses may or may not require positioning of markers or tags on the patient body. That is, the practioner 112 may electronically tag pixels associated with the patient's body. The, recording of the video signal and comparison of the recorded marker pattern with standard patterns are then anaylzed, and therapy, medication, etc. may be prescribed as needed. Visual comparison of video records over time also may tie sufficient or effective to perform diagnosis.

Thus, the video picture or signal alone may be relied upon to provide a medical signal or diagnostic information relating to specific body parts or functions. This results since physician and medical practitioners regularly rely upon visual diagnosis. The system of the invention permits such diagnosis. As another, rather than using a wide angle video input to view the entire patient in an ambulatory condition to study gait, etc., a narrow field or angle signal can be utilized to conduct, for example, an eye examination. Such an examination could focus on eye movement, pupil size under differing conditions, eye reaction time, eye condition in view of a regimen of medication, visual field and numerous other diagnostic matters. The condition and color of skin can also be examined using a narrow field visual technique. Again, the visual condition of a patient is an important diagnostic tool and reaction to medication, growth of moles, and skin disturbances can be recorded, compared to standards and prior data in an ongoing manner to facilitate patient treatment.

The ability of the patient 16 to see and talk to the health practitioner 112, and know that the health practitioner 112 can see the patient 16, is greatly reassuring to elderly patients, or, for that matter, to any patient, and is a significant improvement over prior art monitoring systems.

Figure 7:
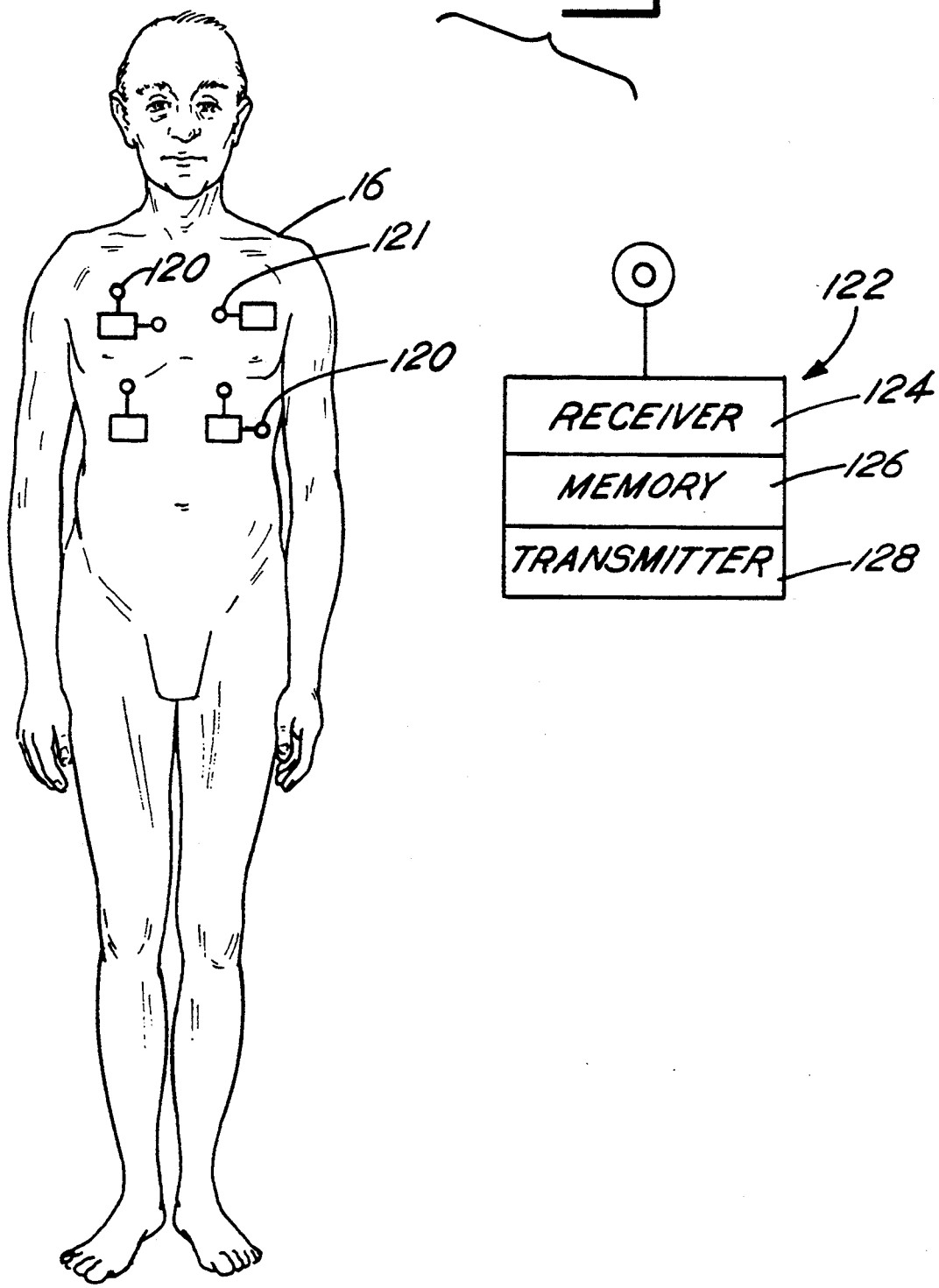
FIG. 7 is an illustration of a health monitoring apparatus which may be used in the present invention in the patient's home environment.

Referring now to FIG. 7, the patient 16 may be a patient with cardiac problems and may be specifically monitored for electrical activity in the heart. The patient 16 has a plurality of miniature electrodes 120 attached to his or her chest which measure the electrical potential on the surface of the chest. The data is transmitted via radio signals emitted by miniature transmitters 121 to a receiver 122. The receiver 122 is typically in the patient's home. The receiver 122 includes a receiver unit 124 and a memory unit 126 including an extended memory for storing transmitted data in a given predetermined period, for example, the previous twelve or twenty-four hours. The receiver 122 also includes a transmission unit 128 which in turn transmits the data directly to the central station 20 preferably through the telephone lines. One advantage of the system of FIG. 7 is that it is a wireless system (i.e., there are no wires from the transmitters 121 to the receivers 122) and thus permits the patient 16 a considerable amount of mobility. Further, there is no heavy or cumbersome equipment to move around. Also, the receiver 122 can be plugged into a standard household wall outlet for power and therefore doesn't require heavy batteries needing frequent replacement. Patient acceptance of the apparatus of FIG. 7 is enhanced because the patient does not look like an astronaut and can participate in his or her usual household activities and interact socially without undue embarrassment, discomfort or inconvenience.

Figure 8:
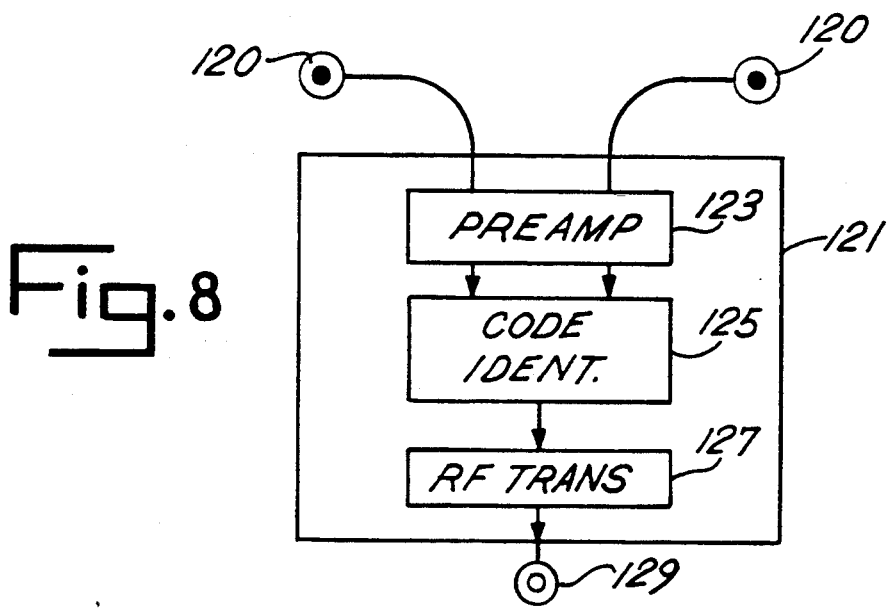
FIG. 8 is a more detailed block diagram of the transmitter of FIG. 7.

FIG. 8 is a more detailed block diagram of the transmitter 121 of FIG. 7. The transmitter 121 is supplied with analog voltage signals from one or a plurality of electrodes 120. The signals from the electrodes are fed to a preamplifier 123 for amplification of the signals. The electrode signals are fed to a code identification unit 125 which identifies the amplified signal with the particular electrode 120. The electrode signals are then supplied to a miniature RF transmitter 127 and antenna 129 for transmission of the signals to the receiver 122 (FIG. 7).

Figure 9:
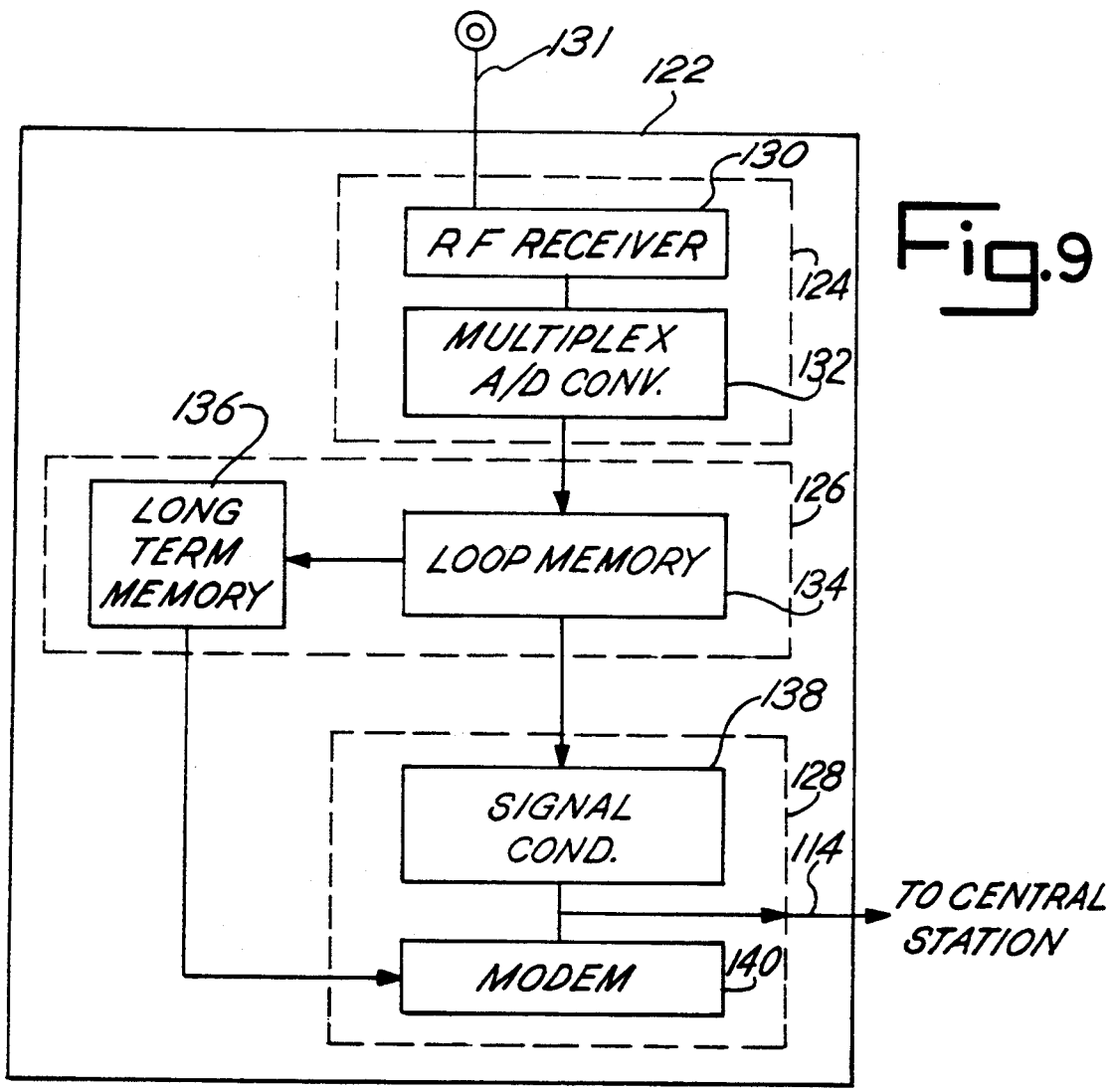
FIG. 9 is a more detailed block diagram of the receiver of FIG. 7.

Referring now to FIG. 9, the receiver unit 124, memory unit 126 and transmission unit 128 of the receiver 122 (FIG. 7) are shown in greater detail. The receiver unit 124 includes an RF antenna 131, a miniature RF receiver 130 and a signal multiplexing and analog-to-digital conversion unit 132. The digital signal is supplied to a loop memory 134 at a sampling rate of 125 Hz. The loop memory 134 with programmable I/O capability stores the digital signal for 10 minute periods and downloads the data in the 10 minute loop memory to a long term (e.g., 24 hour) memory 136, preferably a 15 megabyte solid state memory chip. The loop memory 134 also sends the incoming digital signals to a signal conditioning unit 138 for digital-to-analog conversion and tone modulation for transtelephonic transmission over telephone line 114 to the central station. The long term memory 136 sends the 24 hour data to a modem 140 for transmission to the central station 20 via the telephone line 114. It will of course be appreciated that other organs besides the heart, e.g., the brain, may be monitored by the equipment in FIGS. 7–9.

Referring now to FIG. 10, the modular medical condition sensing and display unit 102 of FIG. 6 is shown in greater detail. The unit 102 has an elongate flexible housing 200 which has a soft and comfortable covering such as cloth or leather. The housing 200 is made flexible so that the unit 102 can securely rest on a variety of surfaces, such as the curved arm 103 of the patient's favorite chair 105, as well as a flat table top or other supporting structure. Built into the housing 200 are a plurality of medical sensors for passively sensing or measuring specific medical parameters.

In the embodiment of FIG. 10, a sensor 204 for measuring the patient's pulse, a sensor 206 for measuring the patient's temperature, and a blood pressure cuff 208 are provided. The sensors in unit 102 may be movable within the housing 200 to accommodate patients with different arm sizes. The sensors 204, 206 and cuff 208 are preferably placed at locations on the upper surface of the housing 200 such that the sensors contact suitable points on the patient's arm when the arm is resting on the housing. Sensors for measuring different parameters could also be provided. The sensors in unit 102 may be movable within the housing 200 to accommodate patients with different arm sizes.

Electrical leads from the sensors are kept out of the patient's way by being led to the interior region of the housing. The leads are supplied to a digital display 210. The digital display 210 has separate screens 212 for display of the temperature, pulse rate, or other parameters sensed by the sensors.

The display 210 is mounted on a hinge 214 such that the display can be oriented vertically. This feature permits the video camera 22 (FIG. 6) to film both the patient and the display 210 without requiring any movement of the camera 22. If the medical data gathered by the sensors 204, 206 is being sent to the central station electronically, or through minitransmitters and receivers, then the display 210 can be folded down out of the way. Should the electronic transmission fail or become interrupted, the display 210 can be pivoted up to face the camera, thereby acting as a backup mechanism.

Referring again to FIG. 6, the use of a video camera 22 in the patient's home is also useful for routine surveillance. For example, the camera 22 permits the monitoring of basic routine activities (washing, dressing, etc.), fluid intake, food intake, and non-medical emergency situations such as threats from the outside (burglars, etc.) and threats from self-inflicted problems (fire, gas leakage, etc.). Interactive visual communication provided by the present invention further helps insure the patient's compliance with prescribed medications, as the health practitioner 112 can actually watch the patient 16 take their pills or other medication.

Though there is depicted a relatively large patient video camera and video receiver in the embodiment of FIG. 6, modern technology will enable reduction of the size of the component parts. For example, a hand held or wrist size screen and transmitter and medical sensor may be used by the patient. Such a combination may be wireless and have the bulk of a cellular phone.

As already noted, one of the main goals of the system is to provide the participants with an inexpensive, simple to use, and versatile home monitoring equipment while the expensive and complex data collection and analysis is performed at the monitoring center. The central monitoring and surveillance could be provided by a private company, which provides around-the-clock monitoring by highly trained nurses. For each participating patient, the monitoring center opens a file in which the general, personal, social, medical, and another relevant data is regularly recorded and compared with data gained by the patient's physician and staff using routine modes of patient care. Alternatively, the central station may be located in a community center or hospital setting.

If cable television is chosen for the communications network 12, 14 (FIG. 1), some components of the interactive audio-visual communication system may be installed by the local cable television operator, such as Cablevision, Inc. The cable television operator typically will install the cable line 48, camera 22 and modulator 46 in the participants' homes, as well as the physicians' remote location 30. The cable television operator may also install the audio-visual equipment, modulator and switching equipment at the central station.

Benefits and Operational Features of the System

1. Improved care for the aged and homebound:

A comprehensive and continuous surveillance system for the geriatric population maintains a good standard of care both in terms of control of daily activities, intake of medications, etc. The ability to anticipate evolving problems and timely intervention capability helps prevent catastrophic medical events, or if they do occur, minimize the health consequences.

2. Psychological Benefits:

In general, the geriatric population suffers from loneliness and anxieties. Elderly people are usually more or less confined to their homes with very little human contact. The proposed system provides the much needed human contact. The possibility of visual and voice contact with the nurses at the central station at any time, day or night, is very comforting to most people in that age group. These people usually form a very close and intimate contact with the monitoring team and they feel as if they belong to a big family of caring individuals.

3. Cost Containment:

The cost-effectiveness of the present ambulatory patient health monitoring techniques is clear. The geriatric population is able to lead independent, more active lives in their own natural environment. There is less need for nursing facilities, geriatric institutions and geriatric beds in hospitals. It is expected that the number of hospitalizations of the elderly will drop and that when hospitalization is still needed, it will be shorter since the patients will arrive at the hospital in a better general condition and return to a controlled environment.

As previously noted, the system includes a simple and relatively inexpensive home medical condition measuring and sensing units and concentrates the expensive equipment in the central surveillance station. This seems to be the only way to provide a cost-effective and maintenance-free system to a large number of elderly persons.

4. Flexibility

The ability to tailor the home monitoring units to the needs of the participant is of great importance. According to the recommendations of the various authorities taking care of the individual, the parameters that need to be monitored are installed and activated. This improves the accuracy of monitoring and reduces cost. The direct, on-line connection between the patient, central station, and the physician permits immediate changes in medications or other treatment regimens as needed thereby avoiding long interim periods of uncertainty. The patients' data file is continually updated providing immediate, up-to-date information to all involved in the care of the elderly person.

Further Considerations

1. Apprehension or resistance to changes:

Changes in personal habits or the introduction of new technology may be met by patients with some apprehension, specifically in the elderly population. Generally, this age group has more difficulty in adapting to new situations. However, television is a very familiar medium to most elderly people and is generally conceived as a friendly medium that helps most elderly pass the time. The addition of interactive capability with health practitioners is generally regarded by the elderly as a blessing rather than a threat. Moreover, the various measuring devices and sensors can be constructed in a manner to demand only minimal or no active participation of the patient. Most elderly persons can cope quite easily with high-tech devices provided operation is kept relatively simple.

2. Privacy:

Fully developed, the system allows health practitioners at the central station to monitor and watch the patient's activities at any time, day or night. The patient and health practitioner may provide that the camera 22 can be turned on remotely from the central station. This may be conceived by the participants as an invasion of their privacy. However, it must be recognized that residents of nursing homes or patients in hospital enjoy only minimal privacy. Nonetheless, the pre, sent invention is a consensual system, and the parties are free to tailor the monitoring how they see fit. The central station could be allowed to initiate audio-visual monitoring only ,during pre-defined conditions (emergency situations, or where certain medical conditions that will call for prolonged monitoring, etc.) if the parties so choose. These specific conditions should be discussed with the participants and the treating physician to avoid any misunderstandings.

CONCLUSION

While the foregoing detailed description sets forth preferably preferred embodiments of the invention, it will be understood that many variations may be made to the embodiments disclosed herein without departing from the true spirit and scope of the invention. For example, it has already been noted that several possibilities exist for the communications network. The particular health monitoring equipment used for measuring medical conditions of the patient in the home may vary widely among the patients. Further, the equipment used in the central station, for example, in the data analysis and display unit, may vary depending on the needs of the patients and the costs which are willing to be absorbed by the participants or operator of the system. This true spirit and scope of the present invention is defined by the appended claims, to be interpreted in light of the foregoing specifications.

What is claimed is:

1. An interactive system for monitoring a patient's condition by a health practitioner, said patient located at a remote location from a central monitoring station and capable of mobility so as to exercise gait, said health practitioner located at the central station, the system comprising:

a) first audio-visual means for generating a first audio-visual signal of said patient at the remote location;

b) means for measuring a medical condition of said patient at the remote location, said means for measuring including means for visually marking specified anatomical locations on the body of said patient for measurement of a gait of said patient;

c) means for generating a :medical signal representative of the measured medical condition, said means for generating including the visual transmission signal of the specified anatomical locations and the changes in said anatomical locations in response to changes in patient location and position within the visual field of the means for generating a visual signal;

d) a central monitoring station;

e) means for transmission of said first audio-visual signal to said central station;

f) means for transmission simultaneously of the medical signal to said central station;

g) display means at said central station for substantially simultaneous display of said first audio-visual signal and said medical signal, said display means further including means for recordal and analysis of the anatomical location measurements of said patient;

h) second audio-visual means for generating a second audio-visual signal of said health practitioner originating from said central station;

i) means for transmission of said second audio-visual signal to said remote location; and j) means for display of said second audio-visual signal at said remote location for observation by the patient simultaneously with transmission of the first audio-visual transmission;

whereby said patient and said health practitioner are capable of substantially simultaneous interactive communication concerning said measured medical condition.

2. The system of claim 1 wherein the means for analysis further includes memory means for recording anatomical location measurements for said patient.

3. The system of claim 2, wherein the means for analysis further includes comparison means for comparing the recorded anatomical location measurements with measurements stored in the memory means.

4. A health monitoring system as set forth in claim 1 further including additional apparatus for monitoring a patient's medical condition in a remote location and for transmission of medical condition information to a central station, comprising:

at least one electrode for attachment to said patient's body;

at least one miniature transmitter receiving signals from said at least one electrode and transmitting said signals; and a receiver comprising a receiver unit for receiving said transmitted signals from said miniature transmitter;

a loop memory for storing said signals for a predetermined short-term time period; and a long-term memory for storing said signals from said loop memory for a long-term time period.

5. A system as set forth in claim 1 further including a modular medical condition sensing and display apparatus for use in a patient's home, comprising, a) a housing suitable for placement on an armrest of a chair;

b) at least one medical condition sensor adapted to said housing for measurement of a medical parameter of said patient when said patient places their arm on said housing; and c) a display attached to said housing for display of said measurement of said medical parameter.

6. The system of claim 5 wherein said display is movably mounted to said housing thereby permitting said display to be moved to a vertical orientation.

7. The system of claim 5 wherein said housing is elongate and flexible, thereby permitting said housing to rest on a wide variety of surfaces.

8. The system of claim 5 wherein said condition sensing and display apparatus further comprise sensors for measuring temperature and blood pressure of said patient.

9. The interactive patient monitoring system of claim 1, further comprising means for remote control from said central station of said first audio-visual means.

10. An interactive system for monitoring a patient's condition by a health practitioner, said patient located at a remote location from a central monitoring station, said health practitioner located at the central station, the system comprising:

a) first audio-visual means for generating a first audio-visual signal of said patient at the remote location;

b) means for measuring a medical condition of said patient at the remote location, said means for measuring including means for visually marking specified anatomical locations on the body of said patient for measurement of the mobility of said patient;

c) means for generating a medical signal representative of the measured medical condition, said means for generating including the visual transmission signal of the specified anatomical locations and the changes in said anatomical locations in response to changes in patient location and position within the visual field of the means for generating a visual signal;

d) a central monitoring station;

e) means for transmission of said first audio-visual signal to said central station;

f) means for transmission simultaneously of the medical signal to said central station;

g) display means at said central station for substantially simultaneous display of said first audio-visual signal and said medical signal, said display means further including means for recordal and analysis of the anatomical location measurements of said patient;

h) second audio-visual means for generating a second audio-visual signal of said health practitioner originating from said central station;

i) means for transmission of said second audio-visual signal to said remote location; and j) means for display of said second audio-visual signal at said remote location for observation by the patient simultaneously with transmission of the first audio-visual transmission;

whereby said patient and said health practitioner are capable of substantially simultaneous interactive communication concerning said measured medical condition.

11. The system of claim 10 wherein the means for analysis further includes memory means for recording anatomical location measurements for said patient.

12. The system of claim 11 wherein the means for analysis further includes comparison means for comparing the recorded anatomical location measurements with measurements stored in the memory means.

13. A system as set forth in claim 10 further including a modular medical condition sensing and display apparatus for use in a patient's home, comprising, a) a housing suitable for placement on an armrest of a chair;

b) at least one medical condition sensor adapted to said housing for measurement of a medical parameter of said patient when said patient places their arm on said housing; and c) a display attached to said housing for display of said measurement of said medical parameter.

14. The system of claim 13 wherein said display is movably mounted to said housing thereby permitting said display to be moved to a vertical orientation.

15. The system of claim 13 wherein said housing is elongate and flexible, thereby permitting said housing to rest on a wide variety of surfaces.

16. The system of claim 13 wherein said condition sensing and display apparatus further comprise sensors for measuring temperature and blood pressure of said patient.

17. The interactive patient monitoring system of claim 10, further comprising means for remote control from said central station of said first audio-visual means.

18. A health monitoring system as set forth in claim 10 further including additional apparatus for monitoring a patient's medical condition in a remote location and for transmission of medical condition information to a central station, comprising:
at least one electrode for attachment to said patient's body;
at least one miniature transmitter receiving signals from said at least one electrode and transmitting said signals; and
a receiver comprising
a receiver unit for receiving said transmitted signals from said miniature transmitter;
a loop memory for storing said signals for a predetermined short-term time period;
a long-term memory for storing said signals from said loop memory for a long-term time period.

19. An interactive system for monitoring a patient's condition by a health practitioner, said patient located at a remote location from a central monitoring station and capable of exhibiting a visual field., said health practitioner located at the central station, the system comprising:
a) first audio-visual means for generating a first audio-visual signal of said patient at the remote location;
b) means for measuring a medical condition of said patient at the remote location, said means for measuring including means for visually marking specified anatomical locations on the body of said patient for measurement of the visual field of said patient.
c) means for generating a medical signal representative of the measured medical condition, said means for generating including the visual transmission signal of the specified anatomical locations and the changes in said anatomical locations in response to changes in patient location and position within the visual field of the means for generating a visual signal;
d) a central monitoring station;
e) means for transmission of said first audio-visual signal to said central station;
f) means for transmission simultaneously of the medical signal to said central station;
g) display means at said central station for substantially simultaneous display of said first audio-visual signal and said medical signal, said display means further including means for recordal and analysis of the anatomical location measurements of said patient;
h) second audio-visual means for generating a second audio-visual signal of said health practitioner originating from said central station;
i) means for transmission of said second audio-visual signal to said remote location; and
j) means for display of said second audio-visual signal at said remote location for observation by the patient simultaneously with transmission of the first audio-visual transmission;
whereby said patient and said health practitioner are capable of substantially simultaneous interactive communication concerning said measured medical condition.

20. The system of claim 19 wherein the means for analysis further includes memory means for recording anatomical location measurements for said patient.

21. The system of claim 20 wherein the means for analysis further includes comparison means for comparing the recorded anatomical location measurements with measurements stored in the memory means.

22. A system as set forth in claim 19 further including a modular medical condition sensing and display apparatus for use in a patient's home, comprising,
a) a housing suitable for placement on an armrest of a chair;
b) at least one medical condition sensor adapted to said housing for measurement of a medical parameter of said patient when said patient places their arm on said housing; and
c) a display attached to said housing for display of said measurement of said medical parameter.

23. The system of claim 22 wherein said display is movably mounted to said housing thereby permitting said display to be moved to a vertical orientation.

24. The system of claim 22 wherein said housing is elongate and flexible, thereby permitting said housing to rest on a wide variety of surfaces.

25. The system of claim 22 wherein said condition sensing and display apparatus further comprise sensors for measuring temperature and blood pressure of said patient.

26. The interactive patient monitoring system of claim 19, further comprising means for remote control from said central station of said first audio-visual means.

27. A health monitoring system as set forth in claim 19 further including additional apparatus for monitoring a patient's medical condition in a remote location and for transmission of medical condition information to a central station, comprising:
at least one electrode for attachment to said patient's body;
at least one miniature transmitter receiving signals from said at least one electrode and transmitting said signals; and
a receiver comprising
a receiver unit for receiving said transmitted signals from said miniature transmitter;
a loop memory for storing said signals for a predetermined short-term time period;
a long-term memory for storing said signals from said loop memory for a long-term time period; and
means for allowing transmission of said signals to said central station.

28. An interactive system for monitoring a patient's condition by a health practitioner, said patient located at a remote location from a central monitoring station, said health practitioner located at the central station, the system comprising:
a) first audio-visual means for generating a first audio-visual signal of said patient at the remote location;
b) means for measuring a medical condition of said patient at the remote location, said means for measuring including means for visually marking specified anatomical locations on the body of said patient for measurement of visual acuity of said patient;

c) means for generating a medical signal representative of the measured medical condition, said means for generating including the visual transmission signal of the specified anatomical locations and the changes in said anatomical locations in response to changes in patient location and position within the visual field of the means for generating a visual signal;

d) a central monitoring station;

e) means for transmission of said first audio-visual signal to said central station;

f) means for transmission simultaneously of the medical signal to said central station;

g) display means at said central station for substantially simultaneous display of said first audio-visual signal and said medical signal, said display means further including means for recordal and analysis of the anatomical location measurements of said patient;

h) second audio-visual means for generating a second audio-visual signal of said health practitioner originating from said central station;

i) means for transmission of said second audio-visual signal to said remote location; and j) means for display of said second audio-visual signal at said remote location for observation by the patient simultaneously with transmission of the first audio-visual transmission;

whereby said patient and said health practitioner are capable of substantially simultaneous interactive communication concerning said measured medical condition.

29. The system of claim 28 wherein the means for analysis further includes memory means for recording anatomical location measurements for said patient.

30. The system of claim 29 wherein the means for analysis further includes comparison means for comparing the recorded anatomical location measurements with measurements stored in the memory means.

31. A system as set forth in claim 28 further including a modular medical condition sensing and display apparatus for use in a patient's home, comprising, in combination, a) a housing suitable for placement on an armrest of a chair;

b) at least one medical condition sensor adapted to said housing for measurement of a medical parameter of said patient when said patient places their arm on said housing; and c) a display attached to said housing for display of said measurement of said medical parameter.

32. The system of claim 31 wherein said display is movably mounted to said housing thereby permitting said display to be moved to a vertical orientation.

33. The system of claim 31 wherein said housing is elongate and flexible, thereby permitting said housing to rest on a wide variety of surfaces.

34. The system of claim 31 wherein said condition sensing and display apparatus further comprise sensors for measuring the temperature and blood pressure of said patient.

35. The interactive patient monitoring system of claim 28, further comprising means for remote control from said central station of said first audio-visual means.

36. A health monitoring system as set forth in claim 28 further including additional apparatus for monitoring a patient's medical condition in a remote location and for transmission of medical condition information to a central station, comprising:

at least one electrode for attachment to said patient's body;

at least one miniature transmitter receiving signals from said at least one electrode and transmitting said signals; and a receiver comprising a receiver unit for receiving said transmitted signals from said miniature transmitter;

a loop memory for storing said signals for a predetermined short-term time period;

a long-term memory for storing said signals from said loop memory for a long-term time period.

* * * * *